(12) United States Patent
Gaffney

(10) Patent No.: US 10,568,784 B2
(45) Date of Patent: Feb. 25, 2020

(54) DISPOSABLE WATERPROOF CAST OR BANDAGE COVER

(71) Applicant: Paul Gaffney, Manchester, NJ (US)

(72) Inventor: Paul Gaffney, Manchester, NJ (US)

( * ) Notice: Subject to any disclaimer, the term of this patent is extended or adjusted under 35 U.S.C. 154(b) by 1034 days.

(21) Appl. No.: 14/542,843

(22) Filed: Nov. 17, 2014

(65) Prior Publication Data

US 2016/0136000 A1    May 19, 2016

(51) Int. Cl.
*A61F 15/00* (2006.01)
*A61F 13/04* (2006.01)

(52) U.S. Cl.
CPC .......... *A61F 15/004* (2013.01); *A61F 13/043* (2013.01)

(58) Field of Classification Search
CPC ...... A61F 13/00; A61F 13/041; A61F 13/043; A61F 15/00; A61F 15/004; A41D 13/00; A41D 13/0543; A41D 13/06; A41D 13/08
USPC ....................................... 602/3; 2/16, 22, 59
See application file for complete search history.

(56) References Cited

U.S. PATENT DOCUMENTS

| | | | | |
|---|---|---|---|---|
| 5,728,052 A | * | 3/1998 | Meehan | A61F 15/004 602/3 |
| 6,512,158 B1 | * | 1/2003 | Dobos | A61F 15/008 602/3 |
| 6,916,301 B1 | * | 7/2005 | Clare | A61F 15/004 128/856 |
| 7,290,290 B2 | * | 11/2007 | Treadway Fancher | A61F 13/06 2/16 |
| 8,056,148 B1 | * | 11/2011 | Ballantyne | A41D 13/08 2/158 |

* cited by examiner

*Primary Examiner* — Keri J Nelson
(74) *Attorney, Agent, or Firm* — Charles Brodsky

(57) ABSTRACT

A plastic sheath dimensioned to fit securely and snugly around an arm or leg cast or bandage of a wearer includes a flexible elastic band at an open first end constructed with at least one expandable trough encircling the sheath, with a stretchable band looped over the elastic band and fitted within the trough at said first end, and with the stretchable band being rollable forwardly from the opened first end of the sheath towards an opposite sealed second end from trough to trough when it is desired to remove the sheath from being worn.

5 Claims, 3 Drawing Sheets

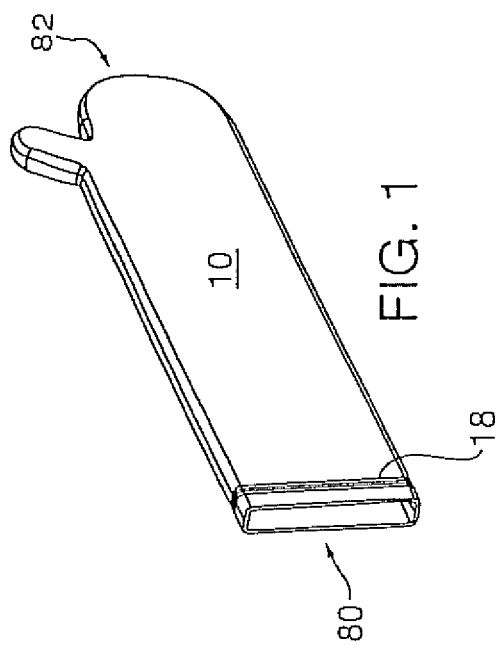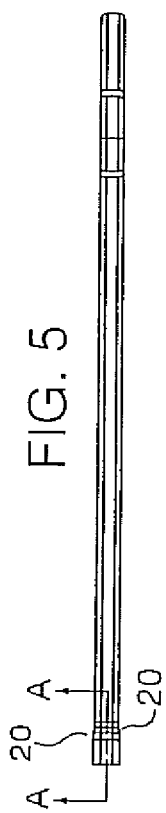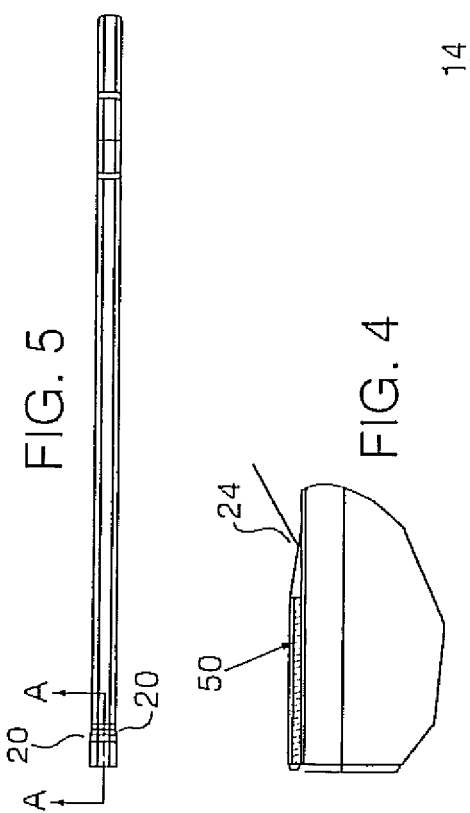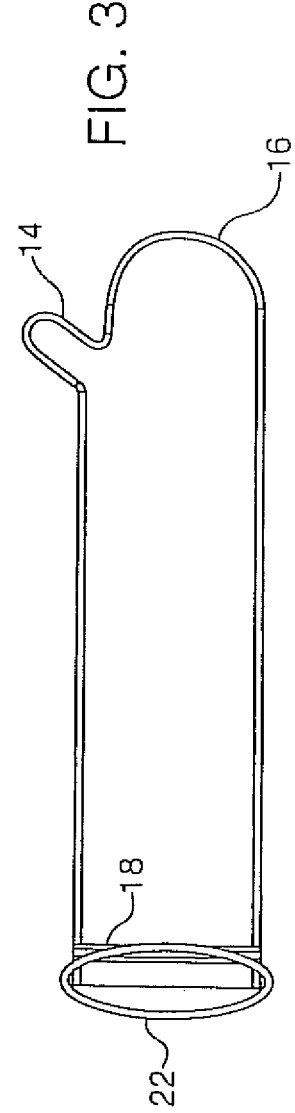

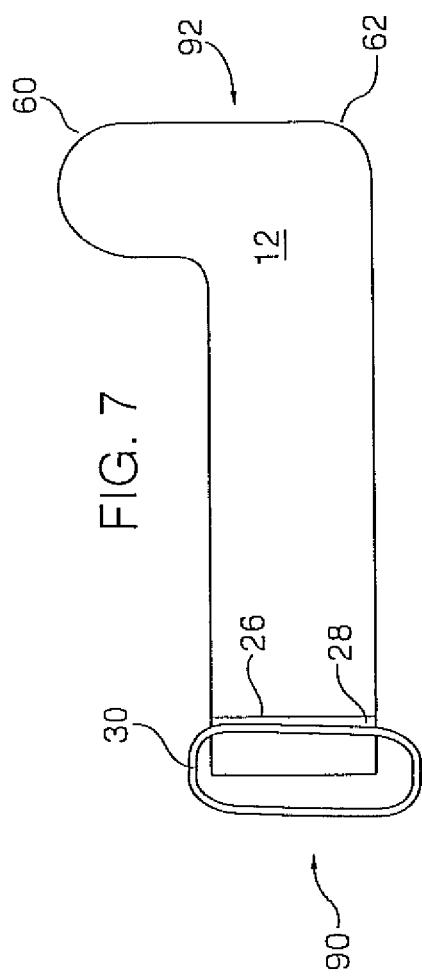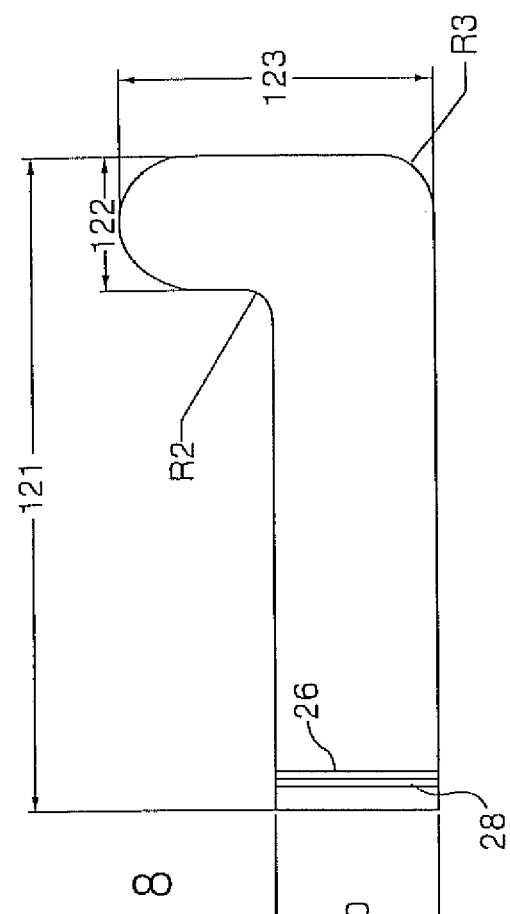

DISPOSABLE WATERPROOF CAST OR BANDAGE COVER

CROSS-REFERENCE TO RELATED APPLICATIONS

A Provisional Patent Application covering the invention described herein was filed on Jun. 2, 2009, and assigned Ser. No. 61/217,525.

This is a Continuation-in-Part of application Ser. No. 12/801,232 entitled Disposable Waterproof Cast or Bandage Cover filed May 28, 2010.

STATEMENT REGARDING FEDERALLY SPONSORED RESEARCH OR DEVELOPMENT

Research and development of this invention and Application have not been federally sponsored, and no rights are given under any Federal program.

REFERENCE TO A MICROFICHE APPENDIX

Not Applicable

BACKGROUND OF THE INVENTION

Field of the Invention

This invention relates to a cast or bandage protector for use when a wearer wishes to bathe, in general, and to such a cast or bandage protector able to be immersed in water, but which is sufficiently inexpensive to allow its being discarded and thrown away after a single use, in particular.

Description of the Related Art

As is understood, cast or bandage protectors are known which comprise elongated bags that fit around the arm or leg of a user to prevent the cast or bandage from getting wet. Primarily used when bathing or showering, these protectors generally are in the configuration of bags that are closed at one end and open at an opposite end. Different types of arrangements have been disclosed to effect a closure of the bag. For example, one construction employs a strap and buckle type of closure. A second employs hook and loop fastener strips in fixing the cover about the extremity being protected. Others utilize overlapping flaps and bands. Still others employ cinch clips, with cords and toothed locking members. These all follow from the recognition that the type of plaster generally used to form a cast around broken or severely injured limbs and joints becomes soft and deteriorates when it gets wet. Patients, therefore, are advised to make every effort to keep the cast (or bandage for that matter) dry at all times.

No matter the type or construction employed, however, the typical approach of an individual who desires to take a bath or shower with a cast or bandage in position is to try to place a plastic bag over the leg or arm, and to then attempt to secure it by tying it around the upper portion of the limb. Although this sometimes provides a satisfactory sealing, experience has shown that the seal, in many instances, still is not effective, and some moisture does, in fact, enter the cast or bandage area. But, almost as equally important is that the prior art covers available are fairly expensive, selling for upwards of $30.00 each, oftentimes as a result of their being designed and constructed for multiple reuse.

Analysis has indicated that a simpler, disposable type of cover would be beneficial to a user if it could provide comparable sealing features and ease in positioning and securing about the limb involved—but one which would be discardable after a single use.

OBJECTS OF THE PRESENT INVENTION

It is an object of the present invention, therefore, to provide a new and improved waterproof cast or bandage cover which fulfills this function, yet one which can be inexpensively manufactured so as to be available for retail sales at a much lower cost.

It is an object of the invention, also, to provide such an improved waterproof cast or bandage cover which can be easily positioned in place by a user, but which is designed and constructed so as to be disposable and easily discardable after use.

It is another object of the invention to provide this waterproof cover in a way as to be easily administrable in conjunction with protecting a cast or bandage on a user's arm or leg, and sufficiently compressible and compactable so as to be able to be packaged several or more to a box, and priced on a per unit basis many times less than that at which the prior art covers are presently being marketed.

SUMMARY OF THE INVENTION

As will be seen from the following description, the disposable waterproof cast and bandage cover of the invention includes a plastic sheath to fit securely and snugly around an arm or leg cast or bandage so as to protect it from water damage. Featuring a flexible elastic band including a first expandable trough encircling the plastic sheath at an open first end of the plastic sheath, a comfortable and secure fit follows through the use of a stretchable band looped over to join and weld the flexible elastic band to the plastic sheath at such open first end. Manufacturable in styles to sufficiently cover full arm and wrist casts, and full leg and foot casts, the waterproof cover of the invention could also be offered in a one-size-fits-all standard for adults—donning the cover over a foot or leg for example as one would do in pulling on a boot—while for an arm, the donning of the cover would mirror the pulling on of a glove, and then upwardly along the arm. A wearer would then be able to take a shower or enjoy a hot bath, while still insuring that the plastic construction of the cover would keep the cast or bandage dry. The flexible elastic band interplay with the plastic sheath would then provide the effective barrier between the water and the protected area.

After the bathing or showering is complete, as will be appreciated, the wearer would simply remove the protector—from the arm or leg by reversing the manner of putting it on, and then dispose and discard the protector instead of hanging it on a towel bar to dry or stowing it in a closet until intended for reuse once again. In this respect, the protector is pulled onto and over an arm or leg cast or bandage of a wearer in securely and snugly fitting the open first end of the plastic sheath of the cast or bandage, while a stretchable band of circular cross section is seated within the first expandable trough of the plastic sheath to enable a removal of the plastic sheath from the cast or bandage by rolling the stretchable band within the expandable trough from its open first end to a sealed second end of the plastic sheath.

BRIEF DESCRIPTION OF THE DRAWINGS

These and other features of the present invention will be more clearly understood from a consideration of the following description, taken in connection with the accompanying Drawings, in which:

FIG. 1 is a perspective view of a waterproof cast or bandage cover for the arm or wrist (hereinafter referred to as a plastic sheath or "glove") constructed in accordance with the teachings of the invention;

FIG. 2 is a right side view of the glove of FIG. 1, a left side view being a mirror image;

FIG. 3 is a top view of the glove of FIG. 1, a bottom view also being in the nature of a mirror image;

FIGS. 4 and 5 are section views of the depictions shown in FIGS. 2 and 3 respectively—FIG. 2 being a sectional view taken along the lines A-A of FIG. 5 and FIG. 4 being an exploded view of the detail A of FIG. 2;

FIG. 7 is a right side view of a waterproof cast or bandage cover for the leg or foot (hereinafter referred to as a "boot") also constructed in accordance with the invention, a left side view being a mirror image; and FIG. 8 is a view helpful in an understanding of the size construction of the waterproof glove of FIG. 7.

DETAILED DESCRIPTION OF THE INVENTION

Figure 6:
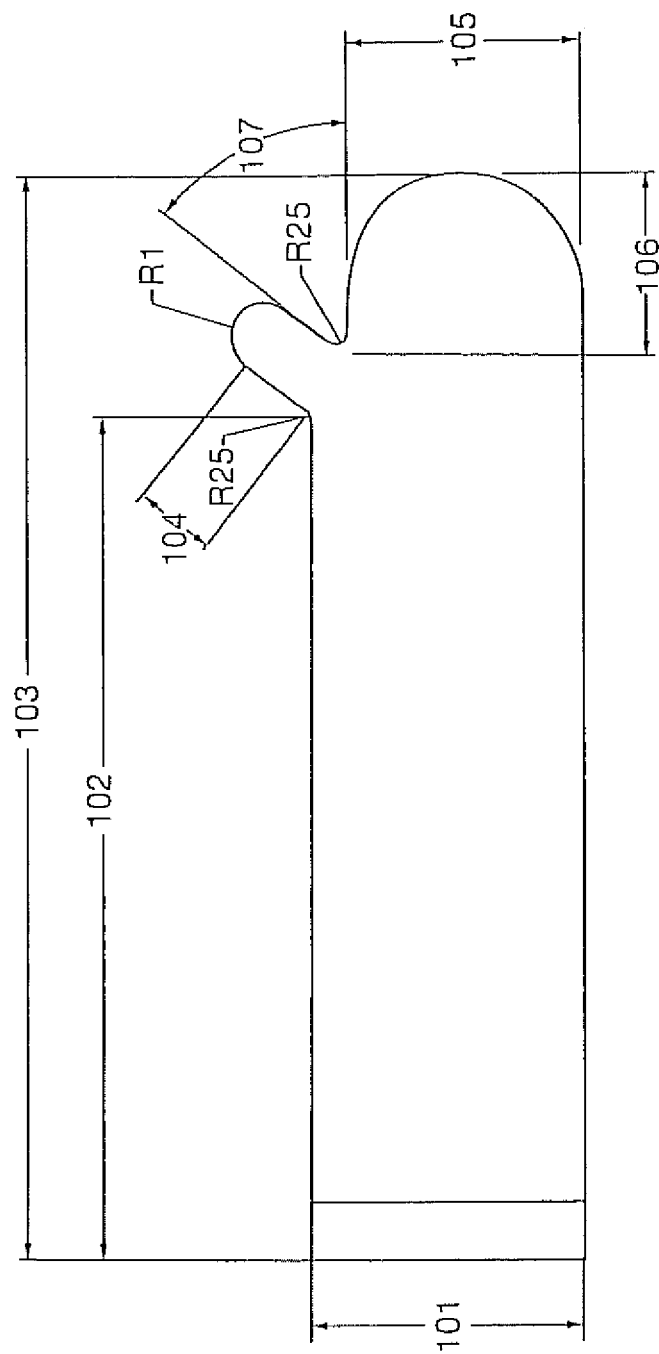
FIG. 6 is a view helpful in an understanding of the size construction of the waterproof glove of FIG. 1.

Both the waterproof glove 10 and waterproof boot 12 of the invention are in the form of a plastic sheath, preferably composed of a polypropylene plastic. The glove 10 of FIGS. 1-6, open at a first end 80 and closed off at a second end 82, is pulled on and then upwardly along the arm in the manner of pulling on the usual type of glove. The boot 12, on the other hand, open at a first end 90 and sealed off and closed at a second end 92, is pulled over a foot or leg as one would normally do in pulling on a boot. The glove 10 includes a segment 14 at the closed end 82 for the insertion of a "thumb" and a segment 16 for inserting the fingers. A flexible elastic band 18 is shown wrapping around at the open end 80 of the glove 10, with the band being provided with one or more expandable troughs 20 encircling the plastic sheath glove (FIG. 5). A stretchable, preferably rubberized band 22 of circular cross section fits over the elastic band 18 to seat within one of the expandable troughs. The elastic band 18 is looped over to join and weld together the flexible elastic band and plastic sheath at 24 (FIG. 4) to complete the seal, as at 50.

The following dimensions have proved useful in a preferred construction of the glove sheath 10:
Dimension 101 . . . 7.5 inches
Dimension 102 . . . 24 inches
Dimension 103 . . . 31 inches
Dimension 104 . . . 2.25 inches
Dimension 105 . . . 7 inches
Dimension 106 . . . 5 inch
Dimension 107 . . . 53°
With the elastic band 18 in place, and with the stretchable band 22 fitted into one of its troughs 20, the glove 10 is secured in place. The glove's polypropylene plastic composition then protects any underlying cast or bandage from becoming wet when the glove is positioned on the user's arm.

The boot 12 of FIGS. 7 and 8 has its own flexible, elastic band 26 at the open first end 90, its own series of one or more expandable troughs 28 immediately adjacent to one another and its own sealing stretchable band 30. The boot 12 includes a segment 60 at its sealed second end 92 for the insertion of the "toes" and a segment 62 for inserting the heel. In its preferred polypropylene plastic manufacture, the following dimensions were effective in providing the waterproof protection:
Dimension 120 . . . 10 inches
Dimension 121 . . . 40 inches
Dimension 122 . . . 8 inches
Dimension 123 . . . 19 inches As will be appreciated by those skilled in the art, once the glove 10 or boot 12 is in position on the arm or leg as the case may be, removal of the glove or boot follows simply by rolling the stretchable band from one trough to another, or just rolling the stretchable band along in constructions where only a single trough is present. However, in both configurations, the waterproof sealing remains in protecting the cast or bandage from getting wet when bathing or showering. Afterwards, the stretchable band is simply removed, and the glove 10 or boot 12 is discarded and disposed of. By virtue of its circular cross section, the rolling off of the stretchable band from the open first end of the plastic glove sheath to the sealed second end of the sheath is easily accomplished.

While there have been described what are considered to be preferred embodiments of the present invention, it will be understood that modifications may be made by those skilled in the art without departing from the scope of the teachings herein. For at least such reason, therefore, resort should be had to the claims appended hereto for a true understanding of the invention.

I claim:

1. A disposable waterproof cast or bandage cover comprising:
   a plastic sheath dimensioned to fit around an arm or leg cast or bandage of a wearer, said plastic sheath having an open first end and a sealed second end opposite thereto;
   a flexible elastic band including a first expandable trough encircling said plastic sheath at said open first end of said plastic sheath;
   a stretchable band of circular cross section seated within said expandable trough of said flexible elastic band at said open first end of said plastic sheath; and
   a loop over and joining together weld of said flexible elastic band with said stretchable band within, said expandable trough to said plastic sheath at said open first end of said plastic sheath;
   with said plastic sheath being of a polypropylene composition, with said stretchable band being of a length and stretch characteristic to enable a pulling of said plastic sheath onto an arm or leg cast or bandage of the wearer in securely and snugly fitting said open first end of said plastic sheath thereabout in use, and with said stretchable band being of a circular cross section to effect a removal of said plastic sheath therefrom by rolling said circular cross section stretchable band within said expandable trough, along and in a direction from said open first end of said plastic sheath to said sealed second end of said plastic sheath, to be removed thereat from the arm or leg of the wearer for discarding after a single use.

2. The disposable waterproof cast or bandage cover of claim 1 wherein said flexible elastic band includes a second, immediately adjacently positioned expandable trough encircling said plastic sheath, wherein said stretchable band is adapted to be fitted within said first expandable trough of said flexible elastic band when said plastic sheath is pulled onto the arm or leg cast or bandage of the wearer, and wherein said plastic sheath is adapted to be removed therefrom by rolling said circular cross section stretchable band from said first expandable trough in which said stretchable band is fitted to said second immediately adjacently positioned expandable trough, proceeding in a direction from said open first end of said plastic sheath along and towards said sealed second end of said plastic sheath.

3. The disposable waterproof cast or bandage cover of claim 2 wherein said plastic sheath includes a first segment of said sealed second end of said plastic sheath adapted for inserting a thumb of the wearer's hand and a second segment at said sealed second end of said plastic sheath adapted for inserting the fingers of the wearer's hand.

4. The disposable waterproof cast or bandage cover of claim 2 wherein said plastic sheath includes a first segment at said sealed second end of said plastic sheath acclimate for inserting toes of the wearer's foot and a second segment at said sealed second end of said plastic sheath adapted for inserting the heel of the wearer's foot.

5. The disposable waterproof case or bandage cover of claim 1 wherein said stretchable band is of rubberized composition.

* * * * *